United States Patent [19]

Cowley et al.

[11] Patent Number: 4,828,798
[45] Date of Patent: May 9, 1989

[54] ON SITE VESSEL CONTENTS ANALYZER

[75] Inventors: Terry W. Cowley, Lake Jackson; Allen R. Faulk, Jr., Freeport; Charles R. Knode, Angleton, all of Tex.

[73] Assignee: The Dow Chemical Company, Midland, Mich.

[21] Appl. No.: 117,179

[22] Filed: Nov. 4, 1987

[51] Int. Cl.[4] ............... G01N 21/00; G01N 9/30; G01N 31/00; G01N 33/00

[52] U.S. Cl. ..................... 422/62; 422/70; 436/167

[58] Field of Search ............ 436/55, 167, 171; 422/62, 70; 55/67

[56] References Cited

U.S. PATENT DOCUMENTS 4,251,503  2/1981  Swindells et al. ............ 436/55
4,592,9703 7/1985  Girling et al. ............... 436/55

Primary Examiner—Barry S. Richman
Assistant Examiner—Lyle Alfandary-Alexander
Attorney, Agent, or Firm—Joe R. Prieto

[57] ABSTRACT

The present invention is directed to a system apparatus and method for on site analysis and identification of the last contents of a container such as tank cars and tank trucks. A sample of gas from the container containing a vaporous sample compound to be analyzed is passed to a gas chromatograph for analyzing the vaporous compound of interest and the data from the gas chromatograph is automatically transferred to a computer controller and data processor, and the data collected by the computer is compared to known standards of a previously identified known vaporous products.

8 Claims, 3 Drawing Sheets

ON SITE VESSEL CONTENTS ANALYZER

BACKGROUND OF THE INVENTION

This invention relates to a process and apparatus for identifying chemical components present in a container. More particularly, the present invention relates to analyzing and identifying what was last contained in a vessel or container, i.e., the "last contents" of the container, by analyzing and identifying vapors of residual chemical or chemicals present in a vessel or container.

In the chemical industry transportation of chemical products commonly takes place by train rail cars (tank cars) or by tank trucks. The tanks on the trains or trucks are shipped from one destination to another, emptied of their contents and thereafter, refilled with chemical product for their next shipment or destination. Sometimes a tank car or tank truck can remain idle for long periods of time before they are filled again.

Usually, after unloading the chemicals from a tank car or tank truck, it is desirous to refill the tank with the identical chemical compound. However, it is not uncommon in the industry to fill a tank car or tank truck with more than one different chemical after several transportations. Usually a residual of chemicals remains in the tank after its contents are emptied and vapors of the chemical compound are formed in the tank. In such an instance, the tank must be checked to verify that the desired chemical to be added to the tank is compatible with the vapors in the tank so that the combination will not cause unwanted contamination, violent reactions or hazards such as explosions. It is also not uncommon in the industry to use other company's tank cars by leasing arrangements. In such instances, in order to avoid the problems enumerated above, it is essential to verify that the chemical compound or compounds present in the tank are, in fact, the chemicals last shipped before the tank is refilled with the same or compatible chemicals.

In the past, in order to carry out verification of the last contents of a tank car, for example, a tank car operator would have to climb on top of a tank car, manually open the tank car cover and manually take a sample from the tank car using a syringe as a sample container. Sampling of the tank car by the operator was not only dangerous to his safety, but was time consuming and cumbersome. Then the sample container would be taken from the tank car site, in hand by the tank car operator, to a laboratory which could be located a great distance (miles) away from the tank site. Laboratory personnel would then analyze the sample by laboratory methods while the tank car operator waited for the results of the laboratory analysis. When the analysis was complete, the operator would then take the results of the analysis back to the tank site so that the operation of filling the tank car could begin. The overall process of verifying the last contents of a tank car was time consuming and cumbersome and was compounded by the multiplicity of samples that needed to be analyzed.

It is therefore, desired to provide an analysis method and system for analyzing the last contents of a container or vessel which allows data to be processed much quicker than done heretofore and much easier, readily, and simpler than the processes heretofore. It is also desired to provide a simplified process for collecting vital data needed to carry on operations of filling tanks and vessels with chemicals.

SUMMARY OF THE INVENTION

One aspect of the present invention includes a method for analyzing and identifying the last contents of a container including sampling vaporous components present in the container, passing the vaporous sample to a gas chromatographic means for analyzing the vaporous components, automatically transferring data from the gas chromatographic means to a computer controller and data processor means, and comparing the data from the computer controller and data processor means to a known standard of previously identified known vaporous products.

Another aspect of the present invention is directed to a system for analyzing and identifying the last contents of a container including a means for drawing a vaporous sample from a container containing a vaporous sample compound of interest to be analyzed, a means for passing the vaporous sample to a gas chromatographic means for analyzing the vaporous sample, a means for automatically transferring data to a computer controller and data processor means, and a means for comparing the data from the computer controller and data processor means to known standards of previously identified known vaporous products.

DETAILED DESCRIPTION OF THE PREFERRED EMBODIMENTS

Figure 1:
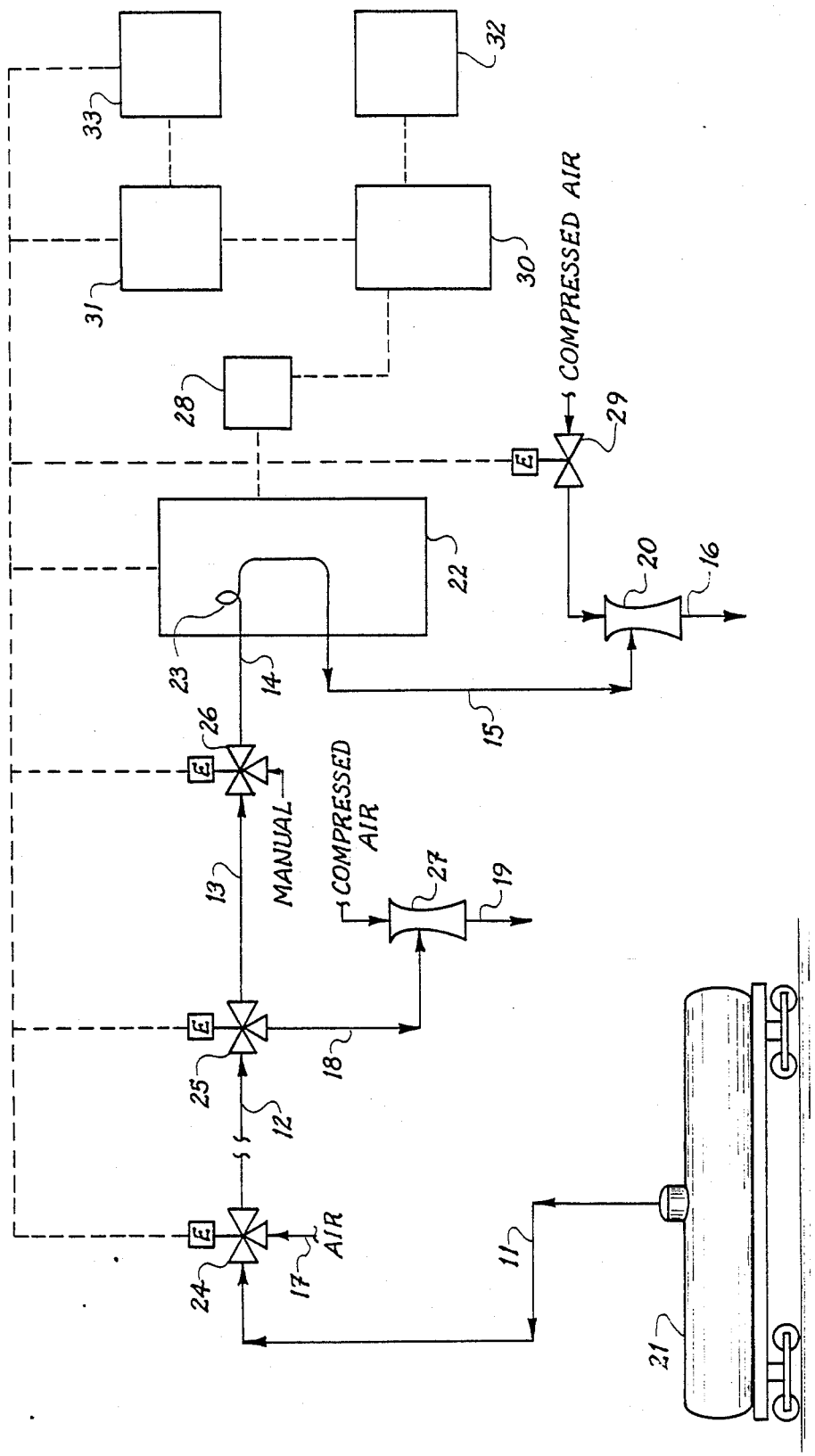
FIG. 1 is a schematic diagram of the apparatus of the present invention.

With reference to FIG. 1, there is shown a system apparatus for analyzing the last contents of a vessel or container 21. The container 21 in FIG. 1 is shown as a tank car 21 and the invention will be described herein with reference to a tank car. However, it is to be understood that the invention is not to be limited to applications wherein a tank car is used.

An aspirator 20 is used for pulling a vacuum on the tank car 21 and carrying a vapor sample from the tank car 21 to and through a gas chromatographic means 22 containing a sample loop 23 via a vapor sample flow line consisting of flow lines 11, 12, 13, 14, 15, and 16. The flow to the gas chromatograph is dependent on the type of aspirator used and is typically advantageous to flow at from about 300 ml/min to about 1500 ml/min and more preferably above about 700 ml/min. The tank car 21 is hooked up to a vapor sample line 11 connected to a three-way solenoid valve 24. In its "open" position the solenoid valve 24 allows a vapor sample from tank 21 through line 11 to pass through to line 12. In its "closed" position the solenoid valve 24 allows air from an air source through line 17 to pass through line 12. Line 12 is connected to a three-way solenoid valve 25 and the solenoid valve 25 is, in turn, connected to line 13 and to an aspirator 27 via line 18. When a sample is not being analyzed, the solenoid valve 25 and aspirator 27 is used to flush sample line 12 from valve 24 to valve 25 and aspirator 27 via lines 17, 12, 18, and 19. After a predetermined amount of sample is passed into the sample loop 23 of the chromatograph 22, a block valve 26 is closed and the lines 11 and 12 are flushed as described above. Substantially simultaneously to closing the valve 26, the air to the aspirator 20 is shut off with valve 29 and analysis of the sample is carried out in the chromatograph 22. After the sample passes through lines 13 and 14 through the gas chromatograph 22, the detector 28 connected to the gas chromatograph 22 sends a signal to a computer controller and data processor means 30 which is connected to a controller means 31. A recording means 32 is also connected to the computer means 30. A monitor 33 is used to monitor the solenoid valves and aspirators.

Sampling of vapor components and analysis of the components is automatically carried out by the system shown in FIG. 1 by starting the computer 30. Optionally, a sample can be manually injected using an injection port provided for, in this instance, in valve 26. After manual injections of the sample using valve 26, the analysis of the vapor components is automatically carried out by the computer controller and data processor 30.

The system shown in FIG. 1 can be used with multiple sample ports or sites. However, only one sample can be analyzed at one time when there is only one gas chromatograph connected to the sample site lines. If desired, multiple gas chromatographs can be connected in parallel for analyzing several samples at one time.

The container to be monitored or analyzed for its last contents can be any container or vessel of industrial or laboratory size and shape which is used for containing chemicals of interest to be analyzed. For example, the container may include storage tanks, tank cars, and tank trucks.

Figure 2:
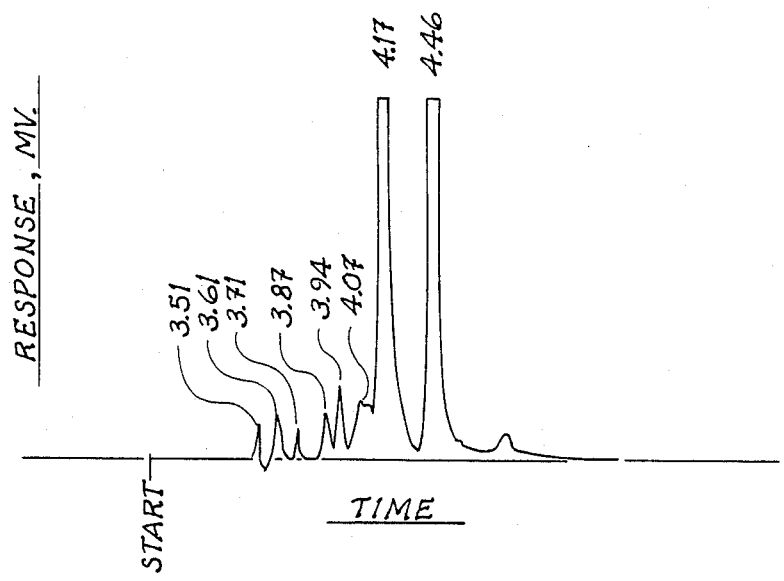
FIG. 2 is a chromatographic scan of the vapor of a compound.
Figure 3:
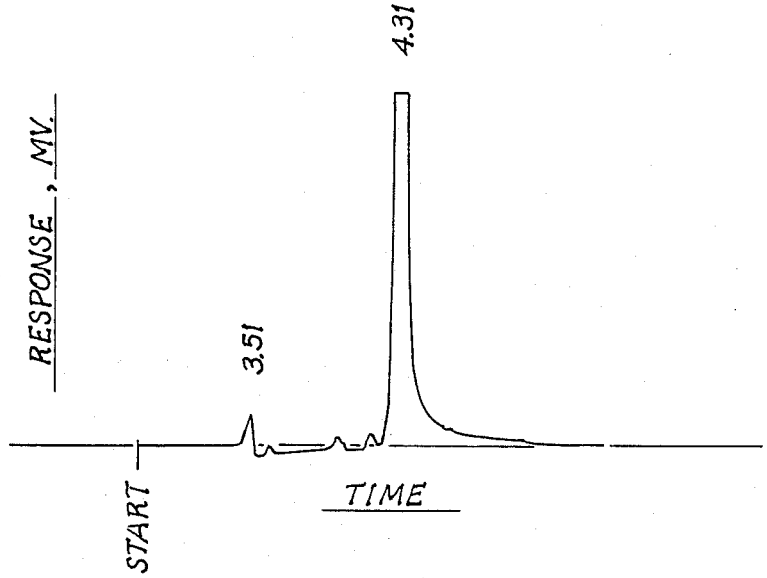
FIG. 3 is a chromatographic scan of the vapor of a compound.
Figure 4:
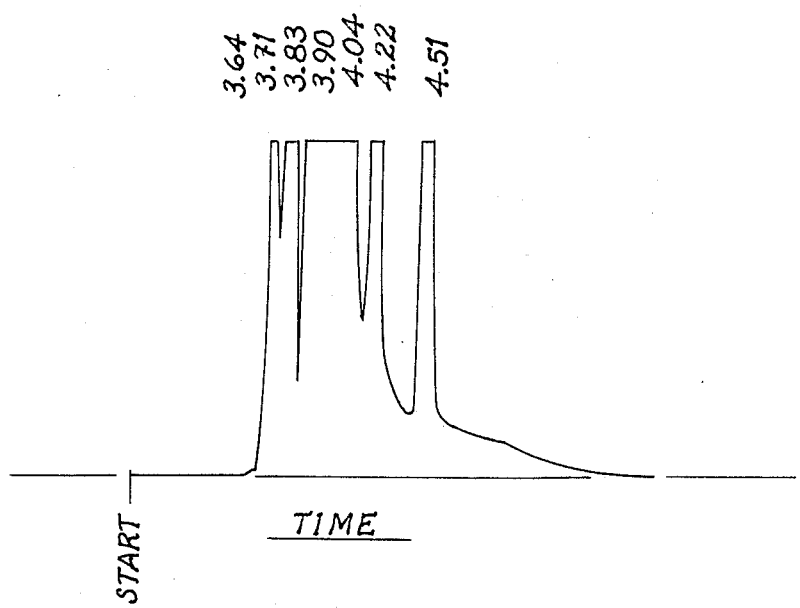
FIG. 4 is a chromatographic scan of the vapor of a compound.
Figure 5:
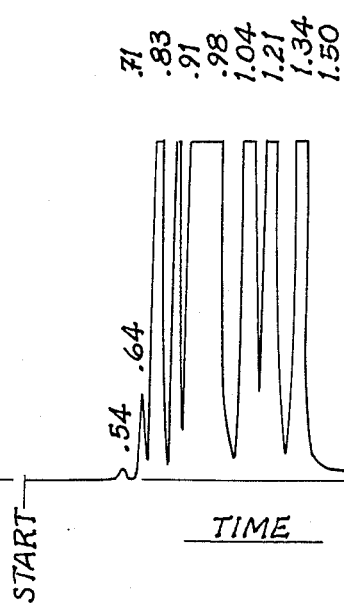
FIG. 5 is a chromatographic scan of the vapors of a mixture of compounds.

The chemicals of interest to be analyzed can be any vaporous or gaseous organic material. The material should preferably have a vapor pressure of 3 mm Hg or greater at about 25 degrees C. Preferably, hydrocarbons are analyzed using the present system. More preferably, chlorinated hydrocarbons such as 1,2,3 trichloropropane, allyl chloride, 2,3 dichloropropene, trans 1,3 dichloropropene, cis 1,3 dichloropropene, propylene dichloride, and epichlorohydrin are advantageously analyzed by the system of the present invention. FIGS. 2-4 are chromatographic scans of the chemicals analyzed by the process of the present invention. FIG. 5 shows that a mixture of compounds of interest could be separated and identified by the chromatograph used in the present invention.

The gas chromatographic means 22 used in the present invention can be any conventional on-stream type gas chromatograph. For example, a commercially available gas chromatograph from Bendix can be used.

The detector 28 used in the present invention can be any conventional detector which will detect the compounds of interest. The vapors of interest in this instance can be detected by a conventional flame ionization detector coupled to the gas chromatograph.

The computer controller and data processor means 30 used in the present invention can also be any conventional piece of equipment known to those of ordinary skill in the art. For example, preferably used is a microprocessor based integrator system, such as an integrator system sold and manufactured by Hewlett-Packard as Hewlett-Packard Integrator 3392A. The integrator allows one to feed in data and desired functions for the integrator to perform and a chart recorder attached to the integrator can record the data received from the chromatographic means for drawing chromatographic scans and calculating the percent area under peaks. The integrator also send a signal to a valve control device or controller means 31 for actuating the opening and closing of solenoid valves and aspirators.

The controller means 31 used in the present invention can be any conventional piece of equipment which is compatible with the integrator above, known to those of ordinary skill in the art. The controller means receives a signal from the integrator 30 and is used for controlling the opening and closing of solenoid valves and aspirators. For example, a controller means sold and manufactured by Hewlett-Packard as Hewlett-Packard 19405A Sampler/Event Control Module can be used.

Any conventional monitoring system may be used to monitor the solenoid valve and aspirator actuation. Optionally, the monitoring unit 33 may allow one to directly energize a solenoid valve of interest manually. The solenoid valve monitor unit lets an operator know what valves and solenoids are open at a given time and allows the operator to manually open or close a valve for trouble shooting.

In another embodiment of the present invention an automatic comparator means can be used for comparing the data received from the chromatographic means to a standard to identify the compounds being analyzed for example by retention time peaks.

EXAMPLE

With reference to FIG. 1, a flow sample line was hooked up to a tank car 21 in the field with the pieces of equipment as shown in FIG. 1. A computer integrator (Hewlett-Packard) was pushed on. The flow of the sample to the chromatograph was about 700 ml/mn. In about 15 minutes the data of analysis of the vapors in the tank car was obtained and the resulting chromatographic scan shown in FIG. 2 was obtained from a chart record built into the computer integrator. The chromatographic scan was visually compared to a standard chromatographic scan previously prepared and was found to be Telone ® II (Trademark of The Dow Chemical Company). The tank car was thereafter loaded with the same Telone ® II compound.

What is claimed is:

1. A process for automatically analyzing and identifying residual vaporous components of interest present in a tank truck or rail car on site of the tank truck or rail car comprising:
   a. providing a compact analyzing means provided with a movable vacuum collecting means capable of collecting vaporous samples whereby the sample is automatically removed from the tank or car and directly transferred to a gas chromatographic separation and analysis means within said compact analyzing means which analyzes the sample and generates analysis data,
   b. taking a sample of the vaporous components present in the tank truck or rail car,
   c. passing the sample through a gas chromatographic means for analyzing the vaporous components for vapors of interest,
   d. automatically transferring the data from the gas chromatographic means to a computer controller and a data processor means, and
   e. comparing the data from the computer controller and the data processor means to a known standard whereby verification of the residual vaporous components of interest is carried out on site of the tank truck or rail car.

2. The process of claim 1 wherein the vapor components are organic vapors.

3. The process of claim 1 wherein the vapor components are hydrocarbons.

4. The process of claim 1 including the step of evaluating the data collected to determine whether or not to load the tank truck or rail car with identical chemical compounds as the vapors of interest.

5. An automated process for analyzing and identifying the last contents of a tank truck or rail car on site of the tank truck or rail car comprising:
   a. providing a compact analyzing means provided with moveable vacuum collecting means capable of collecting vaporous samples whereby the sample is automatically removed from the tank or car and directly transferred to a gas chromatographic separation and analysis means within said compact analyzing means which analyzes the sample and generates analysis data,
   b. the vacuum drawing a vaporous sample of interest from the tank truck or rail car containing the vaporous sample compounds to be analyzed,
   c. passing the vaporous sample containing the vaporous compounds to the gas chromatographic means for analyzing the vaporous compounds,
   d. automatically transferring the data from the gas chromatograph to a computer controller and a data processor means, and
   e. automatically comparing data from the computer controller and the data processor to a known standard of vaporous products whereby verification of the residual vaporous components of interest is carried out on site of the tank truck or rail car.

6. An apparatus for automatically analyzing and identifying the residual vaporous components present in a tank truck or rail car on site of the tank truck or rail car comprising:
   (a) a compact analyzing means with a movable vacuum collecting means capable of collecting vaporous samples whereby the sample is automatically removed from a tank or car and directly transferred to a gas chromatographic separation and anaylsis means within said compact anaylzing means which analyzes the sample and generates analysis data,
   (b) means for automatically transferring the generated data to a computer controller and data processing means, and
   (c) means for automatically comparing the data from the computer controller and the data processor means to a known standard of vaporous products whereby verification of the residual vaporous components of interest is carried out on site of a tank or a car.

7. An automated system for analyzing and identifying the last contents of a tank truck or rail car on site of tank truck or rail car comprising:
   (a) a compact analyzing means with a moveable vaouum collecting means capable of collecting vaporous samples whereby the sample is automatically removed from a tank truck or car and directly transferred to a gas chromatographic separation and analysis means within said compact analyzing means which analyzes the sample and generates analysis data,
   (b) means for automatically transferring the generated data to a computer controller and data processing means, and
   (c) means for automatically comparing the data from the computer controller and the data processor means to a known standard of vaporous products whereby verification of the residual vaporous components of interest is carried out on site of the tank or car.

8. An apparatus for automatically analyzing and identifying the residual vaporous component present in a tank truck or rail car on site of the tank truck or rail car comprising:
   (a) a compact analyzing means with a solenoid valve means for passing a sample through a sample line that is connected to a movable vacuum collecting means capable of drawing the sample through the line whereby the sample is automatically removed from a tank truck or rail car through the line and directly transferred to a gas chromatographic separation and analysis means within said compact analyzing means which analyzes the sample and generates analysis data,
   (b) means for automatically transferring the generated data to a computer controller and data processing means,
   (c) means for automatically comparing the data from the computer controller and the data processor means to a known standard,
   (d) a sampling controller means for actuating the solenoid valve means and the sample vacuum means for controlling the flow of the sample through the line to the chromatographic means, and
   (e) a solenoid monitoring unit for indicating that the solenoid value means and the sample vacuum means are activated whereby verification of the residual vaporous components of interest is carried out on site of the tank or car.

* * * * *